(12) United States Patent
Wyss

(10) Patent No.: US 11,744,914 B2
(45) Date of Patent: Sep. 5, 2023

(54) PROJECTION OF GERMICIDAL ULTRA-VIOLET LIGHT BY EDGELIT SUBSTRATE

(71) Applicant: John R. Wyss, Chehalis, WA (US)

(72) Inventor: John R. Wyss, Chehalis, WA (US)

( * ) Notice: Subject to any disclaimer, the term of this patent is extended or adjusted under 35 U.S.C. 154(b) by 145 days.

(21) Appl. No.: 17/300,426

(22) Filed: Jun. 30, 2021

(65) Prior Publication Data

US 2022/0040361 A1 Feb. 10, 2022

Related U.S. Application Data

(60) Provisional application No. 63/103,096, filed on Jul. 15, 2020.

(51) Int. Cl.
*A61L 9/20* (2006.01)
*A61L 2/10* (2006.01)

(52) U.S. Cl.
CPC ............. *A61L 9/20* (2013.01); *A61L 2209/12* (2013.01)

(58) Field of Classification Search
CPC . A61L 9/20; A61L 2/10; A61L 2/0047; A61L 2202/11; A61L 2209/12
See application file for complete search history.

(56) References Cited

U.S. PATENT DOCUMENTS

| | | | | |
|---|---|---|---|---|
| 3,881,478 A | * | 5/1975 | Rosendahl | A42B 3/24 128/200.28 |
| 4,965,887 A | * | 10/1990 | Paoluccio | G02C 11/00 2/205 |
| 5,048,516 A | * | 9/1991 | Soderberg | A62B 18/003 128/205.25 |
| 5,447,528 A | * | 9/1995 | Gerardo | A42B 1/244 607/91 |
| 6,053,936 A | * | 4/2000 | Koyama | A61M 21/00 600/27 |
| 6,350,275 B1 | * | 2/2002 | Vreman | A61N 5/0601 607/91 |
| 6,416,531 B2 | * | 7/2002 | Chen | A61N 5/0601 604/20 |
| 6,772,762 B2 | * | 8/2004 | Piesinger | A62B 7/00 128/857 |
| 7,234,831 B1 | * | 6/2007 | Hanley | A42B 1/244 2/209.13 |
| 8,733,356 B1 | * | 5/2014 | Roth | A62B 18/003 128/205.27 |
| 9,278,148 B2 | * | 3/2016 | Fewkes | G02B 6/0028 |

(Continued)

*Primary Examiner* — Sean M Luck

(57) ABSTRACT

A novel purification device is provided which projects Ultra-Violet wavelength light to create curtain-like beams that impair germs and pathogens exposed thereto or passing through the beams. A preferred embodiment described herein is comprised of a powered Light Emitting Diode to produce light, mounted edgelight-fashion onto an optically clear substrate light guide that has clear remote outer edges for light projection. Substrate utilized herein is an optically clear sheet such as acrylic that guides the edge-mounted L.E.D. produced Ultra-Violet wavelength light to its remote edges, projecting it outwardly through surrounding air and onto surfaces in light beams emitting from edges of the substrate, projected in suitable strength and wavelength UV-C to create a curtain-like partition, a barrier deadly to airborne or surface germs, and renders germs exposed to the light dead, damaged or inert.

2 Claims, 5 Drawing Sheets

(56) References Cited

U.S. PATENT DOCUMENTS

| | | | |
|---|---|---|---|
| 9,380,822 B2 * | 7/2016 | Foster | A42B 1/18 |
| 9,938,165 B2 * | 4/2018 | Taghipour | C02F 1/725 |
| 10,551,542 B1 * | 2/2020 | Tan | H01L 25/0753 |
| 10,932,513 B1 * | 3/2021 | Day | A42B 1/244 |
| 2005/0078473 A1 * | 4/2005 | Zuloff | A42B 1/004 |
| | | | 362/106 |
| 2007/0133935 A1 * | 6/2007 | Fine | G02B 6/0061 |
| | | | 385/131 |
| 2008/0192458 A1 * | 8/2008 | Li | G02B 6/005 |
| | | | 313/498 |
| 2008/0266839 A1 * | 10/2008 | Claypool | A42B 1/244 |
| | | | 2/209.13 |
| 2009/0025716 A1 * | 1/2009 | Glazman | A62B 18/003 |
| | | | 607/94 |
| 2010/0188340 A1 * | 7/2010 | Smoot | G06F 3/04883 |
| | | | 345/173 |
| 2011/0291995 A1 * | 12/2011 | Shr | E05B 1/0069 |
| | | | 250/492.1 |
| 2012/0182726 A1 * | 7/2012 | King | F21S 9/037 |
| | | | 362/183 |
| 2013/0033895 A1 * | 2/2013 | Brown | G02F 1/1336 |
| | | | 703/1 |
| 2013/0118506 A1 * | 5/2013 | Osipov | A41D 13/1184 |
| | | | 128/858 |
| 2013/0152919 A1 * | 6/2013 | Billingsley | A61M 16/107 |
| | | | 128/201.25 |
| 2014/0052050 A1 * | 2/2014 | Courtin | D03D 15/547 |
| | | | 604/20 |
| 2014/0268683 A1 * | 9/2014 | Waters | A42B 1/244 |
| | | | 362/106 |
| 2014/0286052 A1 * | 9/2014 | McCollum | G02B 6/0078 |
| | | | 362/613 |
| 2015/0037201 A1 * | 2/2015 | Armour | A61B 90/06 |
| | | | 600/203 |
| 2015/0092972 A1 * | 4/2015 | Lai | H04R 1/1083 |
| | | | 381/333 |
| 2016/0066643 A1 * | 3/2016 | Squair | A42B 3/225 |
| | | | 2/424 |
| 2016/0296649 A1 * | 10/2016 | Ramanand | A61L 2/28 |
| 2016/0309826 A1 * | 10/2016 | Anderson | A42B 3/0453 |
| 2016/0310758 A1 * | 10/2016 | Friedman | A61N 5/062 |
| 2017/0242253 A1 * | 8/2017 | Benesh | G02B 27/0172 |
| 2017/0361133 A1 * | 12/2017 | Yu | A61M 16/0066 |
| 2018/0264161 A1 * | 9/2018 | Welch | A41D 13/1192 |
| 2019/0030196 A1 * | 1/2019 | Bilenko | A61L 2/10 |
| 2019/0070326 A1 * | 3/2019 | Xie | A61L 2/26 |
| 2019/0098969 A1 * | 4/2019 | Gibson | F21V 33/0008 |
| 2019/0099613 A1 * | 4/2019 | Estes | A61N 5/0616 |
| 2019/0204602 A1 * | 7/2019 | Wu | G02B 6/0055 |
| 2019/0209857 A1 * | 7/2019 | Brawn | A61C 7/00 |
| 2020/0281686 A1 * | 9/2020 | Finkelstein | A61B 46/20 |
| 2020/0309703 A1 * | 10/2020 | Luk | G01N 21/6486 |
| 2021/0322621 A1 * | 10/2021 | Tillmanns | A61L 9/20 |
| 2021/0353969 A1 * | 11/2021 | Leschinsky | A62B 9/00 |

* cited by examiner

PROJECTION OF GERMICIDAL ULTRA-VIOLET LIGHT BY EDGELIT SUBSTRATE

BACKGROUND

This invention relates to innovations in U.V. light technology for air purification and in light emitting diode (LED) light panel technology. Advances have enabled the use of specialty design to procuce UV-C (germicidal UV) LED lighting which is a primary source of lightwave production in this present invention. The discovery of ultra violet lighting as a defense against pathagens dates back prior to 1903 when a Nobel Prize was awarded to Niels Finsen for his research and discoveries using UV to combat lupus vulgaris, tuburculosis of the skin. More major innovation occurred in the 1950's when advancements in technology improved such that it became useful to apply high intensity UV in the 200 nm-300 nm range to kill germs and sanitize domestic and municipal water in systems for public consumption. Specifically, short-wavelength ultraviolet in this range is referred to as UV-C, and the process of disinfection is generally called UVGI for Ultraviolet Germicidal Irradiation and has been proven to be an effective deterrent to harmful germs such as bacteria, virus, molds and even parasites.

The principles described herein incorporate high-intensity edgelighting concepts that this inventor disclosed and taught in 2013 in U.S. Pat. No. 8,529,113 B2, and are adapted into various embodiments of the present invention. Such as, a method of installing powerful LED lighting onto relatively thin acrylic sheet is enabled by the addition of an optical wedge at the edgelit input area to widen the input edge to accept input from larger LEDs as light is concentrated by the wedge as a lens into the thinner sheet.

Further innovation is present herein, since light remains guided to remote edges of the sheet, and projects outwardly from the edges. Typical L.E.D. panels, monitors and television screens which commonly employ edge-lighting must project light from the front viewing surfaces only and edges are not used for projection. This innovation projects light only from its clear edges. Light loss from front or back of substrate is not desired, so L.E.D. light is guided to the remote edges only.

It is assumed the reader and users have basic knowledge of LED edge-lighting principles, plastics design and UV-C Ultraviolet Germicidal Irradiation in order to understand and achieve the desired effects developed under this novel design for a wide variety of UV purification devices and atmospheric purification systems for area environments, personal protective masking, cubicles, partitions and rooms that are intended to be dis-infected by this invention. Construction of wearable face-shields utilizing suitable acrylic glass substrate is possible in numerous and various ways already well known in prior art.

OBJECTS AND ADVANTAGES OF THE INVENTION

Of particular note is that this is a very uncomplicated device. The present invention provides anew and novel use of UVGI properties of UV-C lightwaves, generated by at least one light emitting diode (LED) of special design which produces 200 nm-300 nm UV light. An object of the invention is to provide an edgelit optical light-guide design to create a UV-C lightwave "curtain" resulting in a projected partition protecting users from airborne pathogens via UV-C germicidal irradiation of air passing through said partition thus providing safe air in an environment protected by said curtain. This method avoids harmful UV contact with the eyes or bodies of its users and adapts to multiple uses and formats including face shields, area partitioning and dis-infection of surfaces.

An objective is to make use of UVGI properties of UV-C lightwaves in a fashion which easily protects users from direct physical contact with UV and prevents damage to skin or eyes which is a known hazard to humans in the proximity of UV waves.

A further object is to provide a novel method for construction of protective face-shielding apparatus to eliminate the need of face mask type coverings in close personal contact situations. A further object is to provide a novel method for the use of UV partitions in creating germ-free spaces, rooms and cubicles.

An advantage of the invention is the adaption of simple UV Light Emitting Diodes. L.E.D.s have advantages over bulkier and less environmentally friendly fluorescent or mercury vapor UV lamps.

Flat beams produced with this method avoids harmful UV contact with eyes or skin of its users through simple lateral shielding at the light source, preventing UV beams from contacting users during normal use. UV is guided through the substrate with nominal losses to the front or rear of the substrate. This method offers multiple uses and formats such as face shields, area partitioning and dis-infection of surfaces.

Other advantages are features like simplicity, low cost, scalability, ease of transport, light weight, availability of components needed for systems and easy training of technicians and contractors installing protective systems in buildings.

SUMMARY OF THE INVENTION

A novel and efficient design is taught herein that relates to UVGI dis-infection of airbourne germs utilizing high intensity UV-C light within the 200 nm-300 nm wavelength range to kill germs. A preferred embodiment is comprised of an electric-powered L.E.D. light source positioned edgelight-fashion upon an optically suitable substrate with which to guide said light, and projects the light from clear edges. Said substrate can be a thin clear sheet of glass or plastic such as methyl methacrylate, also known as acrylic, acrylic glass, or plexiglass, typically at least 1 mm thickness or greater.

"Edgelight-Fashion" refers to the practice of positioning at least one light, generally a strip or bar of powerful lighting, such as L.E.D., along the edge of a relatively flat optically conductive substrate, acrylic or plexiglass-type sheeting, generally having thickness of a millimeter or more, up to any thickness called for by design engineering. The light guidance through said substrate has in the past been diverted by use of light disrupting dots, diffusers or textures, which disrupt guided light from the substrate to exit frontally in order to provide back-lighting for flat screen monitors and television screens. Absent any form of internal light disruption, and with polished outer edges upon the substrate, UV light produced in a predetermined strength and wavelength enters at the source, which is the L.E.D. edgelight, and exits the substrate at its remote polished edges as a relatively flat beam, and projects a "curtain" of UV-C light outward from the edges of substrate. By this process a sanitizing partition beam is created through which air exposed to adequately intense UV-C for sufficient time is dis-infected. So, air passing through the partition beam is sanitized and cleared of harmful germs prior to its direct contact to a user's face or inhalation thereof. Face-shields, masks and U.V. purification, as well as edgelighting of substrates for light panels, monitors and televisions are well known and described in prior art.

An optically conductive substrate lends itself to a simple wearable face-shield device. The flat directional nature of edge-lighting on optically suitable substrates affords the ability to create an UV-C curtain hazardous to germs without directly exposing users eyes or skin to the harmful beams, yet the beams provide partitioned spaces with a boundary of protective curtains wherein air passing through the beams is dis-infected of virtually all airbourne virus, mold spores, bacteria, and germs.

Measures are taken by design to ensure effectiveness of these devices, particularly by the strength of UV-C produced by L.E.D. light at point of input. This is determined by the strength of light at the input edge of the optical substrate. Key effectiveness factors are time of germ exposure to UV-C, and distance from the origin of said UV-C wave source, being most effective close-up and for longer periods of exposure to germs. Clearly, intense UV-C and longer exposure kills germs better.

Motion of the light-wave curtain by "sweeping" the light curtain back-and-forth over areas causes more dis-infection if intensity or time of UV-C exposure is increased upon the germs. Let it suffice to say that power level and specifics, of design should obviously provide the needed and adequate exposure strength and time in order to kill or harm pathogens as desired.

In summary, the invention is a logical step in the direction of improved face shielding and air purification for pathogen protection and dis-infection of local atmospheres by way of U.V. lighting products in general, accommodating key issues such as efficacy, power consumption, cost, portability, convenience, wear-ability, together with additional advantages of simplicity of construction that make use of readily available common items such as acrylic, poly carbonate or plexiglass-style sheeting of suitable optical quality and light emitting diodes of ultra-violet wavelength and adequate strength to kill live pathogens in these new applications.

Drawings illustrating basic devices according to the novel art taught are shown, followed by suggestions of other useful embodiments envisioned. Those with knowledge in the field will anticipate obvious uses which, in the interests of brevity and focus on novelty, are not all illustrated herein.

BRIEF DESCRIPTION OF THE DRAWINGS

FIG. 2.B. illustrates a variation adaptable to any type of hat with a brim, with a truncated light guide substrate.

DRAWINGS AND DESCRIPTION

Simply stated, this is an uncomplicated device. In a basic embodiment, there are only three primary components involved in creation of this purification device:

1) An electrical power supply source, 100, and connecting means, 110, which in the preferred embodiment is of proper voltage and amperage to adequately supply said ultra-violet lighting in edge-light fashion for projection of a UV-C light curtain, for example, many U.V. wavelength L.E.D.'s operate in the range of 4.5 to 20 volts DC, for which numerous forms of direct-current batteries exist and are readily available on the open market.

2) A Light Emitting Diode or a diode-powered light bar, 200, which in the preferred embodiment is at least one L.E.D., and is of high intensity-UV-C light within the 200 nm-300 nm wavelength range and of adequate power to kill germs, mounted in edgelight fashion upon;

3) A suitable optically clear substrate, 300, a light guide having a front side and a backside, such as acrylic or plexiglass sheet or panel with a thickness of 1 mm or more, and having clear outer edges for the acceptance and guidance of input light from the LED, and the projection at clear remote edges of said light in beams to create a UV-C light curtain, 400, which is harmful or deadly to pathogens.

Figure 1A:
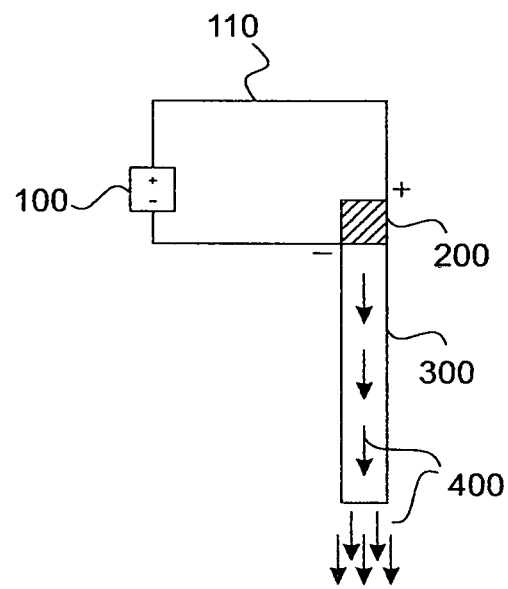
FIG. 1.A. shows a cross-sectional view of an embodiment employing basic construction of the novel device FIG. 1.B. is a second cross-sectional view and illustrates some modifications anticipated, which produce increased efficiency.
Figure 1B:
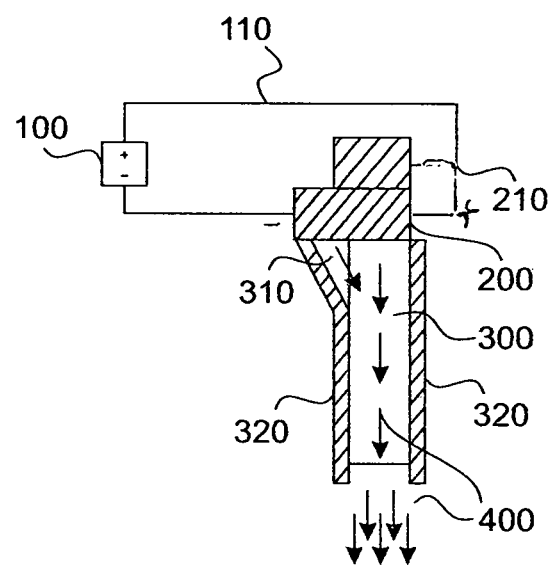
Figure 2A:
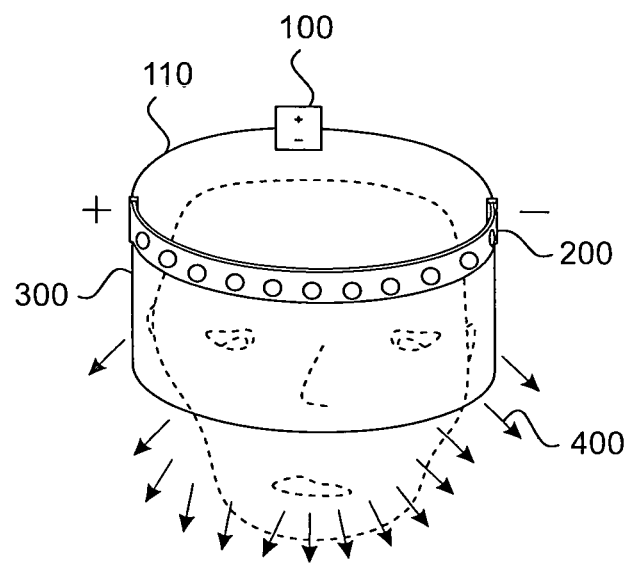
FIG. 2.A. shows a simple face-shield worn over the head having a light system employing the construction of FIG. 1.A.
Figure 2B:
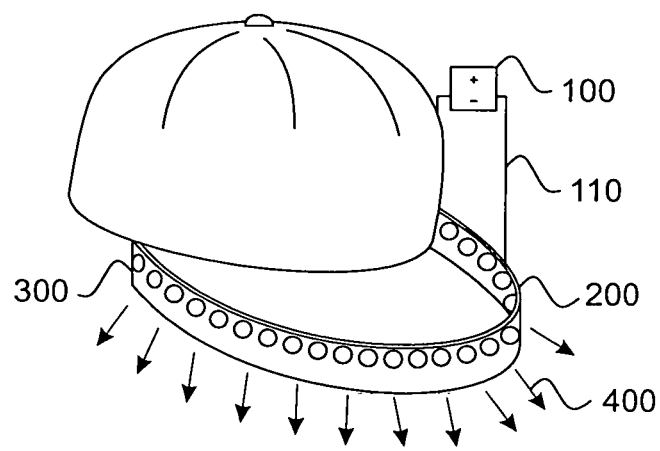
Figure 3A:
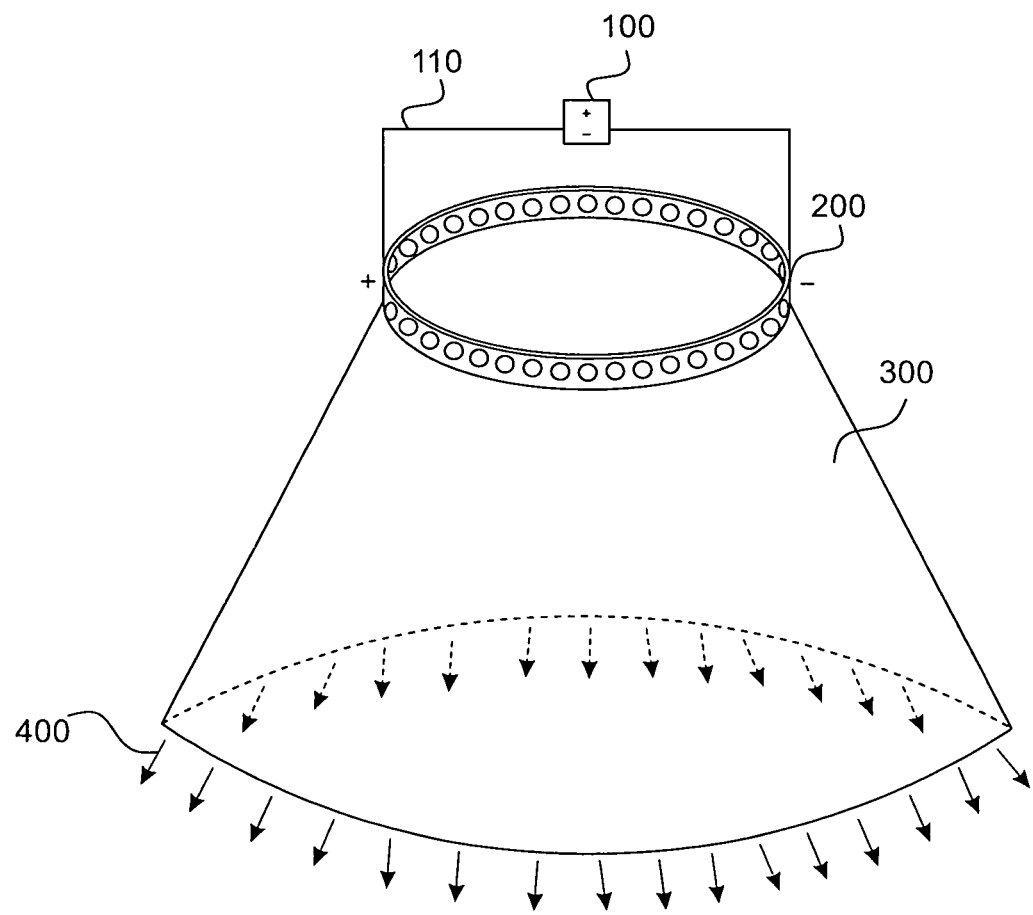
FIG. 3.A., protection of an area where, for example, people may be seated, or an office cubicle. A circular shade or umbrella shaped light guide FIG. 3.B. shows a light guide substrate, 300, constructed having four sides of optically suitable substrate. Within the perimeters of the four UV curtains, 400, formed within the shade, all who may inhabit benefit from protective dis-infection properties FIG. 4.A., illustrates an application designed as a partition protecting one side from the other is a wall or a shield light guide substrate.
Figure 3B:
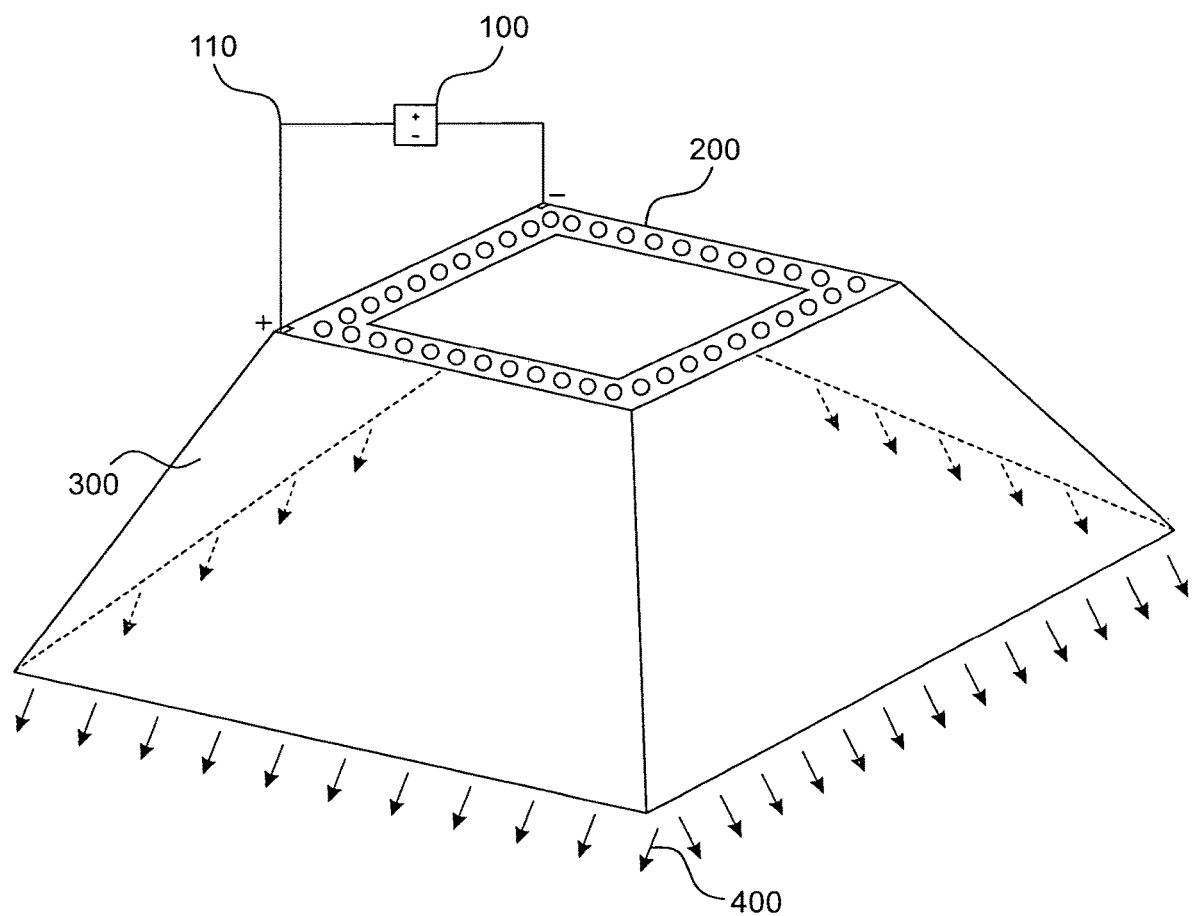
Figure 4A:
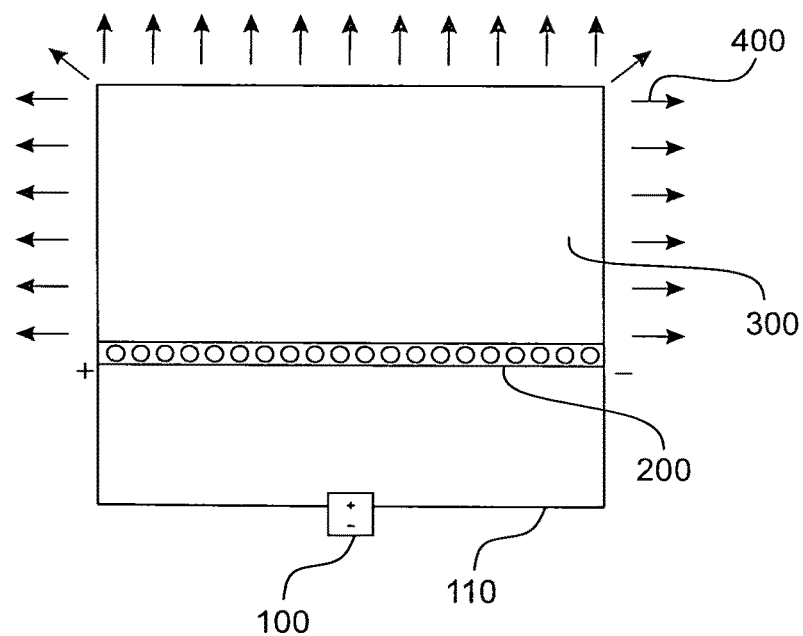
FIG. 4.B. illustrates a further adaption of edgelight technology providing additional flexibility in the positioning and effective closing of all gaps in protection of a defined atmosphere.
Figure 4B:
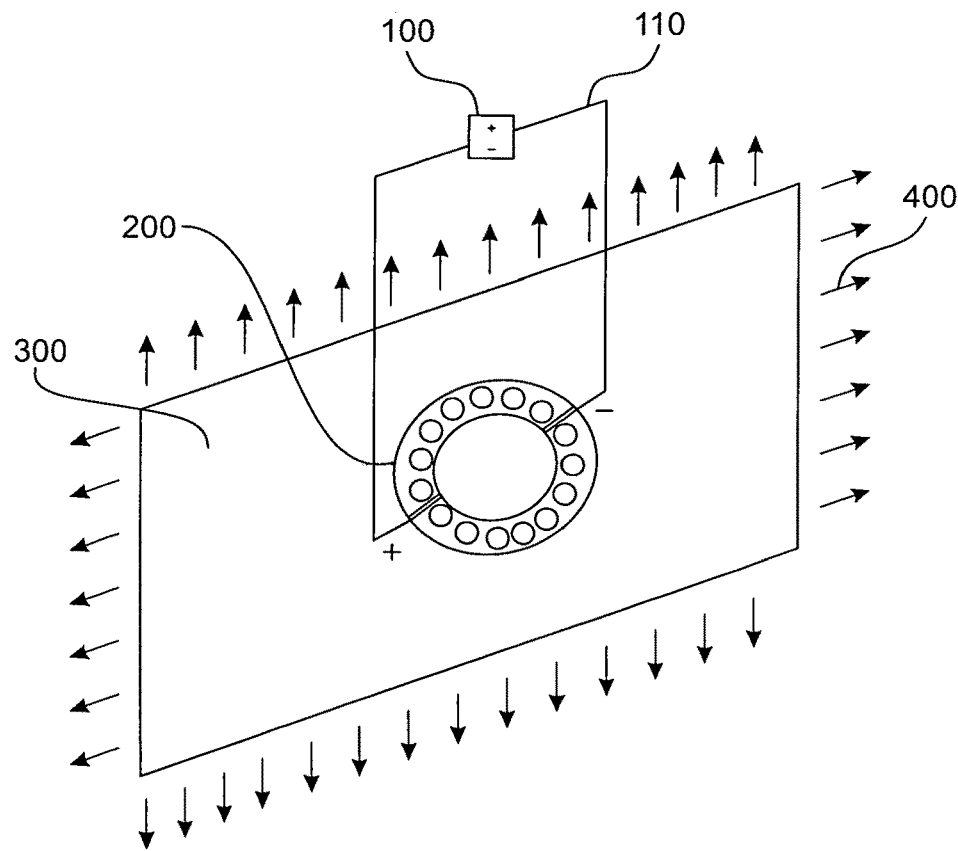

Now we must examine the illustrations:

FIG. 1.A. shows a cross-sectional view of an embodiment employing basic construction of the novel device and is comprised of:

An electrical power supply source, 100, of sufficient voltage and amperage, connected by wiring, 110, to;

An ultra-violet wavelength producing light emitting diode, 200, of high intensity UV-C light within the 200 nm-300 nm wavelength range and of adequate power to kill germs, mounted in edgelight fashion upon;

A suitable optically conductive substrate material, 300, a clear sheet having clear or polished edges for light input, guidance and outward projection of UV-C light, 400, from its remote edges. In this embodiment, an acrylic sheet, 300, with thickness of at least 1 mm and clear edges for input from said L.E.D., 200, and clear edges for light projection is employed;

Projected UV-C germicidal light beams, 400, of 200 nm to 300 nm, collectively create the desired germicidal UV-C light curtain, 400, neutraling germs contacting the curtain.

FIG. 1.B. is a second cross-sectional view, and illustrates some modifications anticipated which produce increased efficiency:

An optically clear substrate sheet or panel, 300, wherein a "light wedge", 310, as described and taught in 2013 in U.S. Pat. No. 8,529,113 B2, by the present inventor, is adapted as an upgrade to the present invention. A properly fitted light wedge integrates with the substrate sheet and creates a wider edge surface along the light input edge;

A wider, larger and stronger light emitting diode, 200, can be edge mounted while not increasing the overall thickness of the primary sheet or panel of clear substrate, 300, and thus greatly increases the intensity and efficacy of the light beam projections, 400, emitted from the optically conductive substrate, 300, of this dis-infecting device whereby UV light emits from clear remote outer edges;

A heat sink is also shown, 210, as a larger and more powerful L.E.D. presence may generate significantly more heat in this embodiment wherein a larger diode, 200, is employed;

A power supply, 100, with wiring connections, 110, supplying proper voltage and amperage is obviously necessary in order to adequately supply said UV-C light beams strong enough to effectively clear live airborne pathogens with beams, 400;

Reflective layers, 320, on both sides of the substrate, 300, increase light guidance efficiency as these layers prevent light losses and the light is now completely guided towards the remote edges, whereupon its exit and projection from said edges form the desired dis-infecting germicidal curtain, 400.

Both examples, when powered, project UV light beams, 400, from outer edges of the substrate, and create UV light curtains, 400, with the specific effect of rendering airborne or surface viral, bacterial or mold pathogens contacted by the curtain, 400, to be damaged and harmless to users of these devices.

We next examine the illustration of FIG. 2.A., a simple face-shield worn over the head having a light system employing construction of FIG. 1.A. above, whereas a face-shield would cover some of the wearer's face. This shows how a substrate piece, 300, a face-shield, wraps about a wearer's forehead and a row of L.E.D.s, 200, would be mounted at the top so as to shine downward into the face-shield sheet, 300, or substrate, from the top and results in a light curtain, 400, out of the bottom edge, as shown in FIG. 1.A., the cut-away view. Light, 400, shines down and out of the bottom of the face-shield. Emitted light, 400, will extend outward in conformance to the lower edge of substrate, 300, from side to side in front of user's face and so dis-infects live air-bourne pathogens which pass through the light beams, 400, prior to their contact with the user's face.

The illustration of FIG. 2.B. is a variation adaptable to any type hat with a brim, with truncated light guide substrate, 300, extending down from the brim just an inch or so, an anticipated use of the technology as a germ shield whereby light creates a curtain, 400, which in the proper strength of UV-C projection dis-infect live air-bourne pathogens passing through said curtain, 400, prior to contacting the user's face.

Following are various embodiments all having similar components.

We next examine the illustration of FIG. 3.A., protection of an area where, for example, people may be seated, or an office cubicle. A circular shade or umbrella shaped light guide, 300, to project said curtain of U.V. purifying light in a way which forms a cone-like area of protected air in an environment around an area, and users may gather and all would receive benefits of protection by the projected light curtain, 400.

We next examine the illustration of FIG. 3.B. where light guide substrate, 300, is constructed having four sides of optically suitable substrate. Within the perimeters of the four UV curtains, 400, formed within the shade, all who may inhabit benefit from protective dis-infection properties We next examine the illustration of FIG. 4.A., an application designed as a partition protecting one side from the other is a wall or a shield light guide substrate, 300, easily adapting the U.V. L.E.D., 200, edgelighting to create a U.V. lightwave curtain of pathogen protection which no live viral threat can cross or pass through, and protects each side from transferred pathogens from individuals on one side to others across the U.V. light curtain, 400.

We next examine the illustration of FIG. 4.B. A further adaption of edgelight technology providing additional flexibility in the positioning and effective closing of all gaps in protection of a defined atmosphere. A center-mounted U.V. L.E.D., 200, gives a 360 degree curtain of protection. For example, partitioning and shielding one entire side of a room from another simply by positioning a center-lit substrate, 300, so a U.V. curtain, 400, extends from floor to ceiling. So, a U.V. curtain, 400, encompass pathways airborne pathogens may cross and thereby provides protection by creating a partition curtain, 400, which pathogens die crossing.

Note that all cited embodiments are comprised of the following basic components which create the desired effect:

A power supply, 100, having any means of electrical connection, 110, together with;

At least one light emitting diode, 200;

A suitable light guide substrate, 300, clear at edges for input light on a clear edge, and projected light which exits the substrate at clear remote edges and thus enables;

The desired effect, being a projected light curtain, 400.

The examples illustrate a partial range of embodiments in various shapes and sizes of optically suitable substrates that lend themselves to a variety of applications and provide airbourne germicidal dis-infection benefits for its users as described herein. It is anticipated that many obvious applications may be adapted, but any light curtain projection device of this type uses the technology described herein.

I claim:

1. A hat, comprising:

a brim;

a light guide substrate coupled and extending downward from the brim, the light substrate substantially covering an edge of the brim;

a power source; and

UV-C LEDs operably coupled to the power source, mounted at an upper end of the light guide substrate, the LEDs operable to shine downward in the light guide substrate, giving a curtain of UV-C light in a front of a user's face.

2. A face shield, comprising:

a light guide substrate coupled and extending downward from the brim, the light substrate substantially covering an edge of the brim;

a power source; and

UV-C LEDs operably coupled to the power source, mounted at an upper end of the light guide substrate, the LEDs operable to shine downward in the light guide substrate, giving a curtain of UV-C light in a front of a user's face.

* * * * *